United States Patent [19]

Darko

[11] 4,443,472
[45] Apr. 17, 1984

[54] METHOD OF TREATING MAMMALS FOR EFFECTS OF NEURO- AND CARDIOVASCULAR TOXINS

[75] Inventor: Laszlo L. Darko, Redding, Conn.

[73] Assignee: Richter Gedeon Vegyeszeti Gyar R.T., Budapest, Hungary

[21] Appl. No.: 358,191

[22] Filed: Mar. 15, 1982

[51] Int. Cl.³ .................. A61K 31/36; A61K 35/78
[52] U.S. Cl. ............................ 424/282; 424/195
[58] Field of Search ........................ 424/282, 195

[56] References Cited

PUBLICATIONS

CA 98:50322a.
CA 98:89040g.

Primary Examiner—Stanley J. Friedman
Assistant Examiner—Freda Abramson
Attorney, Agent, or Firm—Thomas E. Spath

[57] ABSTRACT

Methods of treating mammals, including man, for poisonous snake and insect bites, *E. coli* endotoxins, botulism and other neurotoxins and cardiovascular toxins by administering therapeutic quantities of physiologically active compounds of the formula:

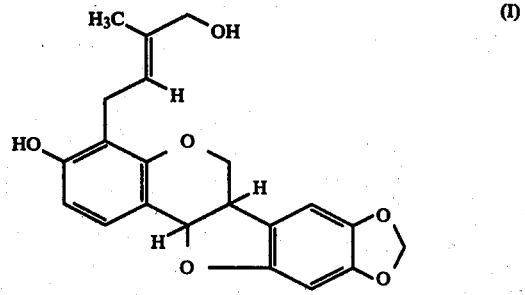

and

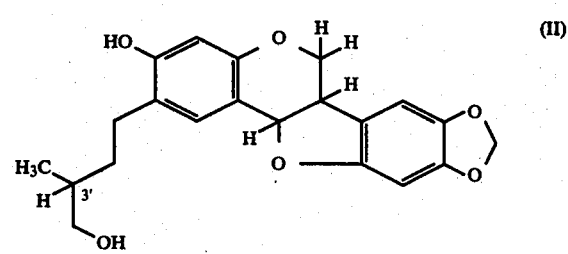

and the materials from which they are derived.

4 Claims, No Drawings

METHOD OF TREATING MAMMALS FOR EFFECTS OF NEURO- AND CARDIOVASCULAR TOXINS

BACKGROUND OF THE INVENTION

FIELD OF THE INVENTION

This invention relates to antidotes for treating the effects of poisonous snake and insect bites in mammals, including man. It also relates to the use of products of manufacture in the treatment of pathogenic bacterial toxins such as E. coli endotoxins, botulism and others which exhibit central nervous system effects and related respiratory paralysis, and to the treatment of the effects of cardiovascular toxins on mammals with the products of manufacture and with aqueous alcoholic extracts of the natural products from which they are derived.

SUMMARY OF THE INVENTION

The invention includes therapeutically active compositions for the treatment of mammals comprising compounds selected from the class of:

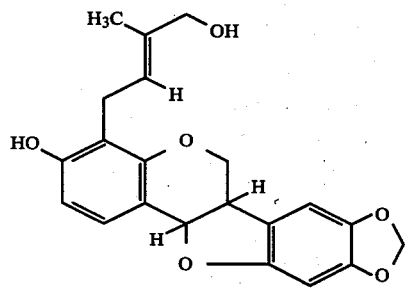

(I)

and

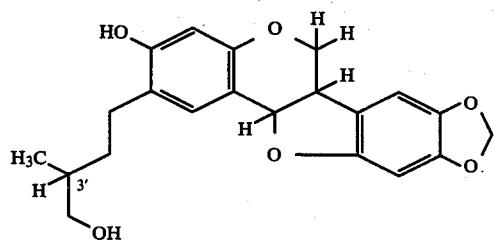

(II)

and pharmaceutical carriers. The invention also includes methods of treating mammals for the effects of neuro toxins and cardiovascular toxins which comprise administering to a mammal a therapeutic quantity of a composition consisting of compounds selected from the class of compounds (I) and (II) set forth above and pharmaceutical carriers. The invention disclosed herein also includes the treatment of specific symptoms in mammals, including humans, with the aqueous alcoholic extracts, or their equivalents, of the natural materials from which they are derived.

The methods for producing cabenegrin I and cabenegrin II in substantially pure crystalline form are described in a co-pending application filed concurrently herewith in the names of Laszlo Darko, Koji Nakanishi and Masachi Nakagawa, under U.S. Ser. No. 357,805, entitled Physiologically Active Compounds and Their Isolation, and the entire disclosure of that application is incorporated herein by reference. That application describes in detail an extraction scheme whereby, as new products of manufacture, crystalline compounds corresponding to compounds (I) and (II) and referred to as cabenegrin I and cabenegrin II, respectively, are obtained, that scheme may be summarized as follows:

About one-half kilo of the cleaned root from the cabeca de negra tree is chopped and further comminuted to break down the fibrous structure. The pulverized root is placed in a container with a sufficient quantity of ethanol:water (77:33) to cover it, and allow to stand, with occasional stirring for about two days. The aqueous alcoholic solution is separated from the root and reduced by gentle warming under vacuum by to brown oily residue. This concentrate is treated with 50% aqueous methanol and the solution extracted with hexane. The hexane layer is discarded and the water layer is extracted with ether. After separation the ether layer is subjected to high pressure liquid chromatography (HPLC) on a column of Sephadex LH-20 and silica gel, using aqueous methanol as the eluting solvent. Two fractions are obtained. The first fraction is subjected to further HPLC and compounds (I), also referred to as cabenegrin I, is obtained as a substantially pure white crystalline material having a sharp melting point at 167°–168° C. The second fraction described above is an oily material which is subjected to further HPLC and compound (II), also referred to as cabenegrin II, is obtained as a crystalline material.

In the above extraction scheme, the presence of physiologically active compounds was determined by in vivo tests employing mice. Test animals were Swiss Webster white mice, mixed sexes, weighing from 20-25 grams. Each group of test animals was envenomated with two and one-half times the lethal dose of snake venom from the Fer de Lance (*Bothrops atrox*) by intraperitoneal injection. In the absence of treatment, envenomated animals succumbed within a few minutes.

Concentrates or compounds (I) and (II) obtained from each of the fractions of the above extraction scheme were tested for antidotal activity by injecting the mice immediately after envenomation with an aqueous ethanol solution (77:23) of the material isolated from each fraction. Each animal was treated with 0.25 ml of the respective solutions. On the basis of this protocol, the minimum dosage for survival against the Fer de Lance venom was 2.8 mg/kg of cabenegrin I and 2.0 mg/kg of cabenegrin II.

Toxicological studies indicate that administration of aqueous ethanolic solutions of cabenegrin I and cabenegrin II to healthy test animals produce no significant changes in vital physiological functions. Administration can be by intravenous or intra muscular injection, or orally via a stomach tube. No significant change is noted in arterial blood pressure, heart rate, respiration, EKG or central venous pressure at any time following administration of compounds I and II to normal, healthy (i.e., non-envenomated) animals.

Administration does not significantly alter resting action potentials, end plate potentials, nerve impulse transmission, neuro-muscular function or brain wave activity in experimental animals.

The following tests demonstrate the treatment with cabenegrin I and II of the effects of toxins which affect either the cardiovascular and/or the neurophysiological systems of experimental animals.

ANTIDOTAL EFFECTS AGAINST SNAKE VENOM IN DOGS

Envenomation by a lethal dose of snake venom, such as *Bothrops atrox, Crotalus adamamteuns,* or *Crotalus atrox,* produces a precipitous fall in arterial blood pressure, a decrease of heart rate and an elevation in central venous pressure. This is followed by partial recovery of these parameters and then by a complete respiratory and cardiovascular collapse. Death appears to be due to a combination or peripheral vascular collapse and to an interruption in the normal respiratory mechanism. In addition, there appears to be some action of these venoms on the central nervous system of the experimental animals. This CNS effect is exhibited by a decrease in both the alpha and the beta rhythm of the brain (EEG). This change is also associated with a decrease in impulse transmission over the motor nerves and progressive blockage of the neuromuscular apparatus which is similar to that produced by curare. Venoms had no effect on muscle response to direct stimulation.

A series of seven adult beagle dogs are used to study the effectiveness of cabenegrin I and II against the venoms. The dogs are anesthetized with Na pentobarbitol (30 mg/kg) and monitored for changes in arterial blood pressure, heart rate, electrocardiogram and respiration. Lethal doses (five to ten times of $LD_{50}$) of lyophilized reconstituted *Bothrops atrox* (Fer de Lance) (2.5 mg–5.0 mg/kg) or (10 mg/kg) South American rattle snake venom are administered.

Within 15 minutes following envenomation, marked decreases in heart rate and blood pressure are consistently noted. At from 15 to 30 minutes, respiration likewise decreases from an average of 20 per minute to 5 per minute. Treatment is initiated when severe cardiovascular embarrassment and apparent respiratory difficulties are observed (usually at from 15–30 minutes following envenomation).

A solution of cabenegrin I is prepared by dissolving 33 mg of the crystalline material of compound in 100 ml of aqueous ethanol (25:75). Similarly, a solution of 24 mg of cabenegrin II in 100 ml of aqueous ethanol (15:75) is prepared. Doses are prepared for administration by stirring 5 ml of each of the respective alcoholic solution of compounds (I) and (II) into 50 ml of water.

Administration of the respective solutions is through a tube placed and advanced into the stomach of the dog. Treatment is as follows: No immediate response is noted following therapy. Blood pressure, heart rate and respiration all remain extremely low. At approximately 30 minutes following the first dose of the respective alcoholic solution of compounds (I) and (II), a slow gradual improvement of breathing occurs followed by partial restoration of heart rate and blood pressure. Continuous therapy is provided at 30 minute intervals in 50 ml water until all monitored vital signs return to within 10% of control.* From two to four doses are required. After observation for 8–10 hours the animals are placed in a holding cage with food and water. At 24 hours, all 7 dogs show signs of depressed activity. At 72 hours, all dogs are taking food and water. No additional therapy is required.

*The effective dose range is between 10 to 20 ml of antivenom extract per animal.

ACTIVITY OF CABENEGRIN II AND II AGAINST *E. COLI* ENDOTOXIN

Three adult beagle dogs are used to demonstrate the effectiveness of the cabenegrin I and II in treating shock caused by *E. coli* endotoxin. The dogs are anesthetized with Na pentabarbital (30 mg/kg) and monitored for changes in arterial blood pressure, heart rate, EKG and respiration. Lethal doses (1 mg/kg) of *E. coli* endotoxin are injected IV into a catheter placed in the vein of the hind limb of the dogs. In the first experiment no antidotal therapy was initiated and the animal expired at 2 hours after injection. In the three additional cases antidotal therapy is initiated at the time when severe cardiovascular collapse and respiratory difficulties appear. These usually occur within about 1½ hours after the injection of the toxin.

Solutions of cabenegrin I and II, prepared as described above, are administered by stomach tube in a single dose of 10 ml in 100 ml of water to each of the dogs. The animals so treated survive and resume normal activity.

ISOLATED HEART (LANGENDORFF) PREPARATION

A series of 2 dog heart preparations are tested to measure the antivenom effect on coronary blood flow, heart rate, EKG, force of ventricular contraction and coronary vascular resistance when cabenegrin I and II are given either before or after lethal venom challenge. It is observed that treatment appears capable of overcoming the toxic effects of the venom on cardiovascular functions. These effects are a decrease of the force of contraction and heart rate. Coronary vascular resistance also increases progressively following the administration of venom. When a solution containing 0.5 mg/ml of either compound (I) or compound (II) are injected directly into the circulation prior to tropical rattle snake venom challenge, no detrimental effect on the heart is observed. Rather, the force of contraction and coronary blood flow increases by about 15 to 20 percent.

When either compound (I) or compound (II) is given following lethal challenge of tropical rattle snake venom, the antidote restores force of contraction and heart rate to normal levels and reverses the minor arrhythmias caused by envenomation.

NEUROPHYSIOLOGICAL FUNCTION

Three dogs and one cat are tested for the antidotal effect on neuromuscular function, action potential and brain wave activity following envenomation with lethal doses of Fer de Lance venom.

Snake venom decreases both brain wave activity and nerve impulse transmission. These are restored to near, if not completely, normal levels by the administration of cabenegrin I and II. Action potentials and neuromuscular function remain depressed for approximately 30 to 60 minutes after treatment with each of the compounds. This is followed by a slow, gradual return to control levels at from 12 to 24 hours.

In certain experiments in which complete neuromuscular blockage occurs and the animals are no longer capable of spontaneous respiration, artificial ventilation is required until the action of the compound has manifested itself. This may occur after envenomation, but once stabilized, the animals are capable of spontaneous breathing and no further therapy is required.

Cortical electrical activity is markedly (25–35%) depressed by the venom. These changes are restored to normal by the administration of the compounds cabenegrin I and II. Following treatment, no further changes are noted.

Results of these studies indicate that oral or IV doses of cabenegrin I and II are capable of treating conditions clinically thought of as being either cardiotoxic and/or neurotoxic in nature with no inherent observable side effects.

Suitable pharmaceutical carriers for oral administration include liquids which are bland to the gastric mucosa. Liquid carriers can be of the type in which a stable suspension of compounds I and II can be prepared. Alternatively, the liquid carrier can be a solvent for the cabenegrin I and II. In the latter case, the liquid pharmaceutical carrier solution can be prepared for either oral administration, or for parental injection.

Novel compositions for oral administration can also be prepared by blending cabenegrin I and II with appropriate dry pharmaceutical carriers known to the art. These dry compositions can be put into any suitable dosage form for ingestion including pills, tablets and capsules. Micro-encapsulation techniques can be employed to provide a sustained release of the desired dosage if the particular condition of the subject indicates this form of therapy.

In many instances, either the nature of the poisonous toxin, or the type or deteriorated condition of the subject will necessitate that a liquid dosage be administered to insure a prompt initiation of the therapeutic effects of the compounds. Effective treatment of animals or of subjects that are unconscious or whose vital signs are in an advanced stage of deterioration will require administration of oral doses via stomach tube or intravenous injection by syringe or catheter.

A pharmaceutical composition was prepared by blending the following materials in the specified proportions by weight:

Compound I: 20
Starch: 15.0
Magnesium stearate: 2.0
Sodium benzoate: 6.0
Benzalkonium chloride: 2.0

After the dry composition was throughly blended tablets were prepared from the mixture. Each tablet was formed so that it contained 100 mg of compound (I). Similarly, tablets were prepared using the same mixture for the pharmaceutical carrier and the same proportion of compound (II) was substituted for the compound, with each tablet containing 70 mg of compound (I).

What is claimed is:

1. A therapeutic composition in dosage form for oral administration comprising a pharmaceutically acceptable solid or liquid carrier and a compound selected from the group consisting of (I) and (II).

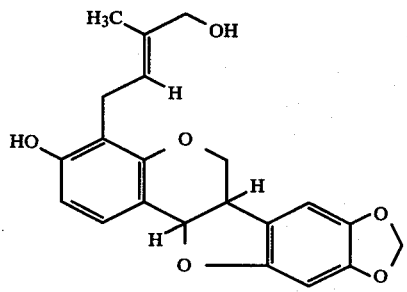

and

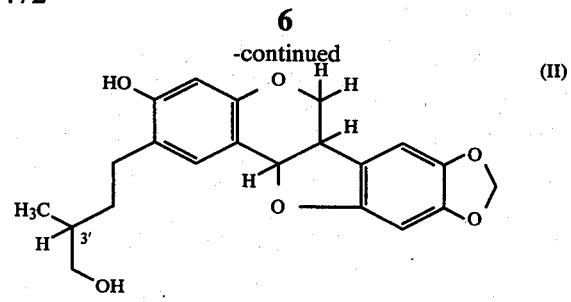

2. A therapeutic composition comprising a pharmaceutically acceptable liquid carrier suitable for parenteral injection in mammals having dissolved therein a compound selected from the group consisting of (I) and (II).

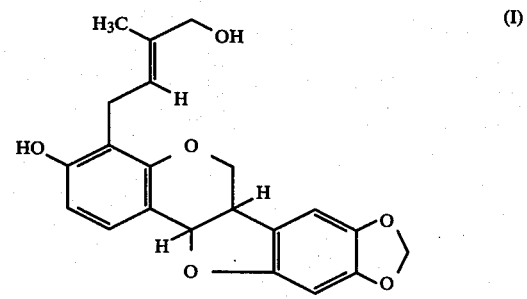

and

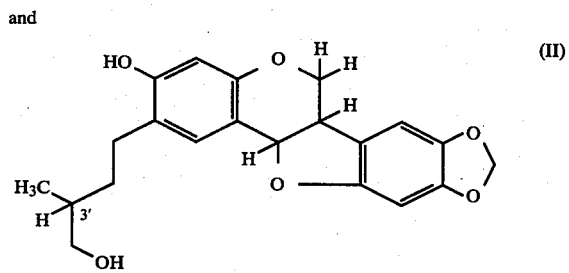

3. A process for treating neurotoxic and cardiotoxic conditions in mammals envenomated by snake venom which consists of administering a therapeutic quantity of a composition comprising a compound selected from the group consisting of (I) and (II).

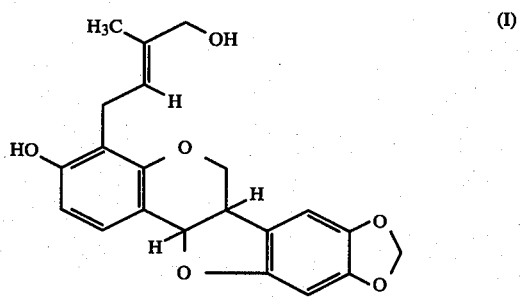

and

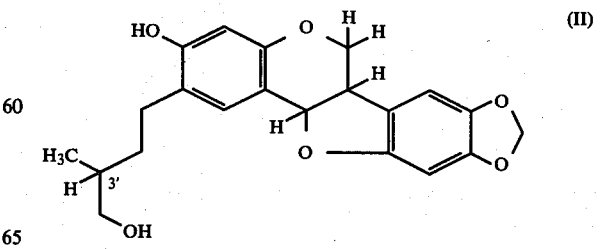

4. The composition of claim 1 wherein the dosage form is a pill, tablet, capsule or solution.

* * * * *

UNITED STATES PATENT AND TRADEMARK OFFICE
CERTIFICATE OF CORRECTION

PATENT NO. : 4,443,472
DATED : April 17, 1984
INVENTOR(S) : Laszlo L. Darko

It is certified that error appears in the above—identified patent and that said Letters Patent is hereby corrected as shown below:

Column 3, line 11 "combination or" should read -- combination of--

Column 3, line 64 should read -- Activity of Cabenegrin I and II --

Column 4, lines 32 and 33 "0.5 mg/m." should read -- 0.05 mg/ml --

Column 5, line 13 should read -- Cabenegrin I or II --

Signed and Sealed this

Thirtieth Day of October 1984

[SEAL]

Attest:

Attesting Officer

GERALD J. MOSSINGHOFF
Commissioner of Patents and Trademarks